(12) United States Patent
Kim et al.

(10) Patent No.: US 9,157,106 B2
(45) Date of Patent: Oct. 13, 2015

(54) POLYNUCLEOTIDE AND USE THEREOF

(71) Applicant: Samsung Electronics Co., Ltd., Suwon-si, Gyeonggi-do (KR)

(72) Inventors: Sea-hee Kim, Seoul (KR); Joo-won Rhee, Yongin-si (KR); Ko-bong Choi, Osan-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 61 days.

(21) Appl. No.: 14/051,259

(22) Filed: Oct. 10, 2013

(65) Prior Publication Data

US 2014/0308709 A1    Oct. 16, 2014

(30) Foreign Application Priority Data

Apr. 15, 2013  (KR) .................. 10-2013-0041255

(51) Int. Cl.
| | |
|---|---|
| *C12P 19/34* | (2006.01) |
| *C12N 15/00* | (2006.01) |
| *C12Q 1/68* | (2006.01) |
| *C12N 15/10* | (2006.01) |

(52) U.S. Cl.
CPC ................. *C12P 19/34* (2013.01); *C12N 15/00* (2013.01); *C12N 15/10* (2013.01); *C12Q 1/6844* (2013.01)

(58) Field of Classification Search
CPC ....................................................... C12P 19/34
USPC ......................................................... 435/91.2
See application file for complete search history.

(56) References Cited

U.S. PATENT DOCUMENTS

| | | |
|---|---|---|
| 6,573,051 B2 | 6/2003 | Alsmadi et al. |
| 6,830,884 B1 | 12/2004 | Hafner et al. |
| 2010/0330619 A1 | 12/2010 | Willis et al. |

FOREIGN PATENT DOCUMENTS

KR      1020090037118 A    4/2009

*Primary Examiner* — Ardin Marschel
(74) *Attorney, Agent, or Firm* — Leydig, Voit & Mayer, Ltd.

(57) ABSTRACT

Provided is a polynucleotide including, from the 3' terminus of the polynucleotide to the 5' terminus of the polynucleotide, a first region including a nucleotide sequence complementary to a nucleotide sequence of a portion of a target nucleic acid; a second region including a nucleotide sequence identical to a nucleotide sequence of a portion of the target nucleic acid; and a third region including a nucleotide sequence that self-hybridizes to form a stem-loop structure, and compositions, kits, and methods related thereto.

17 Claims, 6 Drawing Sheets

POLYNUCLEOTIDE AND USE THEREOF

CROSS-REFERENCE TO RELATED APPLICATIONS

This application claims the benefit of Korean Patent Application No. 10-2013-0041255, filed on Apr. 15, 2013, in the Korean Intellectual Property Office, the entire disclosure of which is incorporated herein by reference.

INCORPORATION BY REFERENCE OF MATERIAL SUBMITTED ELECTRONICALLY

Incorporated by reference in its entirety herein is a computer-readable nucleotide/amino acid sequence listing submitted concurrently herewith and identified as follows: One 1,795 Bytes ASCII (Text) file named "712812_ST25.TXT," created on Oct. 10, 2013.

BACKGROUND

1. Field

The present disclosure relates to a polynucleotide which includes a region complementary to that of a target nucleic acid, a region having the same nucleotide sequence as that of the target nucleic acid, and a region having a stem-loop structure, and a use thereof.

2. Description of the Related Art

In general, samples obtained in the medical field are usually a small amount and present as a mixture containing various kinds of nucleic acids. Therefore, it has been necessary to amplify the amount of target nucleic acid present in a sample for its accurate analysis.

Further, when there is a variation such as a mutation, a deletion, an insertion, a fusion, or an inversion in a specific gene, it is necessary to accurately detect only the specific gene and perform sequencing of the gene to reduce cost. Accordingly, there is a need for the development of a technology for specifically amplifying a disease-specific gene via a sequence-specific amplification.

BRIEF SUMMARY OF THE INVENTION

Provided is a polynucleotide including, from the 3' terminus of the polynucleotide to the 5' terminus of the polynucleotide, a first region including a nucleotide sequence complementary to a nucleotide sequence of a portion of a target nucleic acid; a second region including a nucleotide sequence identical to a nucleotide sequence of a portion of the target nucleic acid; and a third region including a nucleotide sequence that self-hybridizes to form a stem-loop structure.

Provided are compositions and kits for amplifying the target nucleic acid including the polynucleotide.

Provided are methods of amplifying the target nucleic acid using the polynucleotide.

DESCRIPTION OF THE DRAWINGS

These and/or other aspects will become apparent and more readily appreciated from the following description of the embodiments, taken in conjunction with the accompanying drawings of which:

In FIG. 1A, "target-specific sequence" represents a sequence complementary to a region of the target nucleic acid (the first region), "self-hybridization sequence" represents a sequence identical to a portion of the target nucleic acid (the second region), and "stem-loop structure" represents a nucleotide sequence having a stem-loop structure (the third region).

DETAILED DESCRIPTION OF THE INVENTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

One or more embodiments of the present invention will now be described in detail with reference to the following examples. However, these examples are not intended to limit the scope of the one or more embodiments of the present invention.

In an aspect of the present invention, there is a polynucleotide including, from the 3' terminus of the polynucleotide to the 5' terminus of the polynucleotide, a first region including a nucleotide sequence complementary to a nucleotide sequence of a portion of a target nucleic acid; a second region including a nucleotide sequence identical to a nucleotide sequence of a portion of the target nucleic acid; and a third region including a nucleotide sequence that self-hybridizes to form a stem-loop structure. The polynucleotide is useful as a sequencing primer and, therefore, may be referred to as a "primer polynucleotide."

The first region and the second region of the polynucleotide may each comprise at least two nucleotides.

At least two consecutive nucleotides from the 3'-terminus of the first region may be complementary to at least two consecutive nucleotides including the 3'-terminus nucleotides from the 3'-terminus region of the target nucleic acid. In other words, the first region may include a nucleotide sequence complementary to a nucleotide sequence of a corresponding number of consecutive nucleotides at (and including) the 3' terminus of the target nucleic acid (referred to as the first region of the target). The first region may consist of any number of nucleotides ('nt', hereinafter), such as at least 5 nt or at least 10 nt (e.g., 5 nt to 50 nt, 5 nt to 45 nt, 5 nt to 40 nt, 5 nt to 35 nt, 10 nt to 35 nt, or 15 nt to 35 nt). The first region may act as a primer. As used herein, "primer" refers to a single stranded oligonucleotide that may serve as a initiation point for template-dependent DNA synthesis at a suitable temperature, buffer, and conditions (e.g., four different types of nucleoside phosphate and polymerase reaction enzyme). The primer may be hybridized or annealed to a region of a template and form a duplex DNA structure. The suitable hybridization conditions of nucleic acids for forming a duplex DNA are well known in the art. Thus, the first region may bind to the 3' terminal region of the target nucleic acid and provide an initiation point for DNA synthesis in which the remaining portion of the target nucleic acid that is not bound to the first region of the polynucleotide serves as the template.

The second region of the polynucleotide begins at the 5' terminus or end of the first region, or intervening non-hybridizing linker sequence, and includes a sequence of at least two consecutive nucleotides that is the same as the sequence of a corresponding number of consecutive nucleotides (at least two) located at and including the 5'-terminus of the target nucleic acid (referred to as the second region of the target nucleic acid). Thus, the nucleotide sequence of the second region may be, for example, identical to the nucleic acid sequence of a corresponding number of consecutive nucleotides at the 5'-terminal region of a target nucleic acid including the 5'-terminal nucleotide. The second region may consist of any number of nucleotides, such as at least 5 nt or at least 10 nt (e.g., 5 nt to 50 nt, 5 nt to 45 nt, 5 nt to 40 nt, 5 nt to 35 nt, 10 nt to 35 nt, or 15 nt to 35 nt). Whereas the first region of the polynucleotide has a sequence complementary to the 3' region (first region) of the target nucleic acid and acts as a primer, the second region has a nucleotide sequence that is the same (identical) to that of the 5' terminal region (second region) of the target nucleic acid and, preferably, does not hybridize to the target. However, upon extension of the first region of the polynucleotide that serves as a primer using the remaining portion of the target nucleic acid as a template, an extension product is produced having a sequence complementary to the target sequence and, therefore, including a region complementary to the second region of the polynucleotide. This extension product may self-hybridize to the second region of the polynucleotide. The term "hybridization" used herein refers to a binding of nucleotide sequences by a complementary nucleotide sequence. Furthermore, the term "self-hybridization" refers to a hybridization of nucleotide sequences within the same molecule.

The third region of the polynucleotide may include a stem-loop structure, which may be provided by a nucleotide sequence that self-hybridizes to form a stem and loop. The term "stem-loop" used herein refers to a structure formed by an intramolecular base pairing when a nucleotide sequence and a complementary sequence thereof is present in reverse direction in the same strand and a non-complementary sequence is present therebetween in the same strand. The term "stem-loop" may be interchangeable used with other terms such as "hairpin" or "hairpin loop". The length of the nucleotide sequence of the third region may be, for example, in the range from 10 nt to 100 nt, 10 nt to 90 nt, 10 nt to 80 nt, 10 nt to 70 nt, 10 nt to 60 nt, 20 nt to 60 nt, or 25 nt to 60 nt.

The third region may be phosphorylated at its 5'-terminus. An enzyme that phosphorylates 5'-terminus may be any well-known enzyme. For example, the 5'-terminus phosphorylating enzyme may be T4 polynucleotide kinase (T4 PNK) or its variants. The conditions for phosphorylation may be appropriately selected by one of ordinary skill person in the art depending on the enzyme. The phosphorylated 5'-terminus of the third region and the 3'-terminus of the extension product may be ligated together to form a circular polynucleotide.

The third region may include a primer-binding site, a restriction enzyme recognition site, a probe-binding site, or a combination thereof. A primer complementary to the third region may be used for amplification regardless of a target sequence and thus may be used as a universal primer. Restriction enzymes and restriction enzyme recognition sites may be appropriately selected by one of ordinary skill in the art. The term "restriction enzyme" used herein refers to an endonuclease which recognizes a specific nucleotide sequence of DNA and cleaves its double strands. The term "restriction enzyme recognition site" used herein refers to a short sequence of DNA which is recognized by a restriction enzyme. The third region may be used as a probe for confirming the presence of a target nucleic acid in a sample. The third region may be immediately adjacent to the second region, without any linker.

The polynucleotide may include DNA, RNA, Peptide Nucleic Acid (PNA), Locked Nucleic Acid (LNA), or a nucleotide analogue.

In another aspect of the present invention, there is a composition for amplifying the target nucleic acid, including a target nucleic acid and a probe polynucleotide as described herein. All aspects of the target nucleic acid and probe are as previously described herein. Thus, the probe nucleic acid may include, from the 3' terminus of the polynucleotide to the 5' terminus of the polynucleotide, a first region including a nucleotide sequence complementary to a nucleotide sequence of a portion of a target nucleic acid; a second region including a nucleotide sequence identical to a nucleotide sequence of a portion of the target nucleic acid; and a third region including a nucleotide sequence that self-hybridizes to form a stem-loop structure. The target nucleic acid may comprise a first region with a sequence including the 3' terminus of the target nucleic acid that is hybridized to the first region of the probe polynucleotide, and the target nucleic acid comprises a second region with a sequence including the 5' terminus of the target nucleic acid that is identical to the sequence of the second region of the probe polynucleotide. The probe polynucleotide may be separate from the target nucleic acid, or may be hybridized to the target nucleic acid. More specifically, the first region of the probe polynucleotide may be hybridized to a sequence of the target nucleic acid including the 3' terminus of the target nucleic acid.

The target nucleic acid may be DNA, RNA, complementary DNA (cDNA) or the combination thereof. The target nucleic acid may be single stranded or double stranded. The target nucleic acid may include a mutation, a deletion, an insertion, a fusion, or an inversion of a specific gene. The length of the target nucleic acid may be, for example, in the range from 15 nt to 300 nt, 15 nt to 250 nt, 15 nt to 200 nt, 15 nt to 150 nt, 30 nt to 150 nt, or 50 nt to 150 nt. The target nucleic acid may be a short length RNA.

The composition is a composition for amplifying a target nucleic acid. Therefore, the composition may further include other well-known materials required for the amplification of the target nucleic acid. For example, the composition may further include a nucleic acid polymerase, a buffer necessary for its activity, a cofactor, and/or a substrate. The nucleic acid polymerase may be DNA polymerase, RNA polymerase, reverse transcriptase, and a combination thereof. The nucleic acid polymerase may have a strand-displacement activity.

In a further aspect of the present invention, there is a kit for amplifying a target nucleic acid, including a target nucleic acid and a probe polynucleotide as described herein, as well as a nucleic acid polymerase. All aspects of the target nucleic acid and probe are as previously described herein. Thus, the probe nucleic acid may include, from the 3' terminus of the polynucleotide to the 5' terminus of the polynucleotide, a first region including a nucleotide sequence complementary to a nucleotide sequence of a portion of a target nucleic acid; a second region including a nucleotide sequence identical to a nucleotide sequence of a portion of the target nucleic acid;

and a third region including a nucleotide sequence that self-hybridizes to form a stem-loop structure. The target nucleic acid may comprise a first region with a sequence including the 3' terminus of the target nucleic acid that is hybridized to the first region of the probe polynucleotide, and the target nucleic acid comprises a second region with a sequence including the 5' terminus of the target nucleic acid that is identical to the sequence of the second region of the probe polynucleotide. The nucleic acid polymerase may be any of those previously mentioned herein or otherwise known in the art.

The kit may further include a material known to be necessary for the amplification of a target nucleic acid. For example, the kit may further include a buffer, a cofactor, and/or a substrate for the activity of a nucleic acid polymerase.

In a still further aspect of the present invention, there is a method of amplifying a target nucleic acid, including incubating a polynucleotide and a sample including a target nucleic acid to form a hybridized product, wherein the; incubating the hybridized product in the presence of a first nucleic acid polymerase to form a extended product complementary to the target nucleic acid sequence, wherein the extended product includes a nucleotide sequence complementary to the second region of the polynucleotide; incubating the extended product in the presence of a ligase to form a circular extended product; and incubating the circular extended product in the presence of a second nucleic acid polymerase to amplify the target nucleic acid.

The polynucleotide, target nucleic acid, and nucleotide polymerase are as described above.

The sample may be a biological sample. The biological sample may include a sample derived from a virus or an organism. For example, the sample may be blood, saliva, urine, feces, tissue, cells, biopsy material, or a combination thereof. The sample may include a stored biological sample, or DNA or RNA separated therefrom. The stored biological sample may be stored by any known method. The sample may have been stored for more than 1 year, for example, for a period of 1 to 10 years. The template DNA or RNA may be DNA or RNA derived from tissue stored frozen or formalin fixed paraffin embedded tissue stored at room temperature. Methods of separating DNA or RNA from a biological sample and methods of converting RNA into DNA are well known in the art.

The incubation may be performed under conditions suitable for hybridization. The conditions for hybridization of nucleic acids to form a duplex structure are well known to one of ordinary skill in the art. The target nucleic acid and the first region of the polynucleotide, which is complementary to the target nucleic acid, may be hybridized by incubation.

The method may include incubating the hybridized product in the presence of a first nucleic acid polymerase to form a extended product complementary to the target nucleic acid sequence, wherein the extended product includes a nucleotide sequence complementary to a second region of the polynucleotide.

The first nucleic acid polymerase may be a DNA polymerase. For example, the DNA polymerase is DNA polymerase I, Klenow fragment, T4 DNA polymerase, T7 DNA polymerase, or a combination thereof.

The incubation may be performed under conditions suitable for polymerization of nucleic acids. The conditions may be appropriately selected by one of ordinary skill in the art. The incubation may be performed in the presence of the polynucleotide, for example, in the presence of 0.2 mM dNTP mixture and 2.5 unit Klenow fragment, for example, at 37° C. for 30 minutes.

The method may further include cooling the extended product followed by heating to form a self-hybridized extended product, after forming the extended product. When the extension product is heated, it is denatured or melts and may thus be separated from the target nucleic acid. In addition, when the heated extension product is cooled down, the second region of the polynucleotide and the extension product including a sequence complementary to the second region of the polynucleotide may form a base paring within the molecule, and the extension product may be self-hybridized. For example, the reaction mixture may be incubated at 80° C. for 10 minutes, cooled down on ice for 1 to 2 minutes, and then incubated at 37° C. for 20 minutes.

The method may include incubating the extended product in the presence of a ligase to form a circular extended product.

The ligase may be DNA ligase. DNA ligase may be a well-known enzyme in the art. For example, the DNA ligase is T4 DNA ligase, T3 DNA ligase, T7 DNA ligase, *E. coli* DNA ligase, a temperature-stable DNA ligase (e.g., Ampligase® DNA ligase), a single-stranded DNA ligase (e.g., CircLigase™ DNA ligase), or a combination thereof. CircLigase™ single strand DNA Ligase is a thermostable ATP-dependent ligase that catalyzes intramolecular ligation (i.e. circularization) of single strand DNA templates having a 5'-phosphate and a 3'-hydroxyl group.

The incubation may be performed under conditions suitable for ligation. The conditions may be appropriately selected by one of ordinary skill in the art depending on the enzyme selected, for example, in a 1×T4 DNA ligase buffer (50 mM Tris-HCl, 10 mM $MgCl_2$, 1 mM ATP, 10 mM DTT), and 1 μl of T4 DNA ligase at 16° C. for 1 hour.

The method may further include incubating the extended product in the presence of an exonuclease to remove single-stranded DNA, after forming the circular extended product. The exonuclease may be exonuclease I. Exonuclease I removes nucleotides from single-stranded DNA in the 3' to 5' direction. The incubation may be performed in a condition suitable for the activity of the exonuclease, for example, at 37° C. for 30 minutes.

The method may include incubating the circular extended product in the presence of a second nucleic acid polymerase to amplify the target nucleic acid.

The second nucleic acid polymerase may be DNA polymerase. The DNA polymerase may be Bst DNA polymerase, HIV reverse transcriptase, pyrophage 3173 DNA polymerase, Tth polymerase, BcaBEST DNA polymerase, or a combination thereof.

The incubation may be performed under conditions suitable for the activity of the nucleic acid polymerase. The incubation may be performed in the presence of a nucleic acid polymerase, a buffer for the activity of the nucleic acid polymerase, a cofactor, and a substrate. For example, the incubation may be performed in a condition which includes a reverse transcriptase or a material necessary for PCR amplification, for example, at 45° C. in the presence of 25 μl of 1× buffer, 1 pmol amplification primer, 0.1% (w/v) Triton X-100, and 0.5 μl Bst polymerase for 1 hour.

The amplification method may be any known method of amplifying nucleic acid. The amplification may be DNA amplification. The amplification method may be an isothermal or thermal cycling amplification. The isothermal amplification may be rolling circle amplification (RCA), strand-displacement amplification (SDA), multiple-displacement amplification (MDA), or a combination thereof.

The amplification may be performed in the presence of an amplification primer. The amplification primer may be a primer complementary to the third region of the polynucleotide or the extended product. The primer complementary to the third region of the polynucleotide may be a universal primer. The primer complementary to the extension product may be a target sequence-specific primer.

The method may further include incubating a blocking polynucleotide lacking a hydroxyl group at the 3'-terminus thereof and complementary to at least two consecutive nucleotides from the 5'-terminus of the target nucleic acid toward its 5' direction along with a sample containing a target nucleic acid, before forming the extended product. The blocking polynucleotide may prevent elongation by a nucleic acid polymerase.

Reactions involving a polynucleotide according to an embodiment of the present disclosure may be carried out in a single tube. In one embodiment, the polynucleotide may be used to detect a target gene having a single nucleotide polymorphism (SNP), an insertion, a deletion, an inversion or a fusion of a gene. In another embodiment, the polynucleotide may be useful for amplifying a plurality of target nucleic acids, or improving amplification specificity, because the polynucleotide has a sequence complementary to a target sequence and a sequence the same as that of a target sequence. In addition, the target nucleic acid may be amplified at a high amplification rate.

EXAMPLES

Example 1

Preparation of Circular Single Strand DNA Using Target DNAs and Primers 1-1. Preparation of a Target DNA and a Primer
A target DNA and a primer with a 5'-phosphorylated terminus as shown below were prepared by Bioneer Corp.

```
target DNA:
                                        (SEQ ID NO: 1)
5'-pCCCTATAGTGAGTCGTATTACAGCAGATGTGGATCAGCAAGCAGG

AGTATGACGAGTCCGGCCCCTCCATCGTCCACCGCAAATGTTCTAGGCG

GACTAT GACTTAGTTGCGTTACACCC-3' primer:
                                        (SEQ ID NO: 2)
5'-pGGGTTGCTGGGGGCGATTGAATCGCCCCCAGCAACCCCCCTATAG

TGAGTCGTATTACGGGTGTA ACGCAACTAAGTC-3'
```

In the target DNA, the region indicated in bold letters represents a region complementary to the first region of the primer, and the underlined region represents a region having the same sequence as that of the second region of the primer. Meanwhile, in the primer, the region indicated in bold letters indicates a first region, the underlined region indicates a second region, and the region not underlined and in bold indicates a third region with a stem-loop structure.

1-2. Preparation of a Circular Single Strand DNA
50 ng of the target DNA and 150 ng of the primer were mixed in the presence of 1×NEB2 buffer solution (50 mM NaCl, 10 mM Tris-HCl, 10 mM MgCl₂, 1 mM dithiothreitol (DTT)). The mixture was incubated at 80° C. for 10 minutes, and then cooled down on ice for 1 to 2 minutes. The mixture was added with 0.5 µl of 2 mM dNTP mixture and 2.5 units of Klenow fragment (NEB), adjusted to a final volume of 5 µl by adding distilled water, and incubated at 37° C. for 30 minutes to extend the target DNA.

The reactants were incubated at 80° C. for 10 minutes, cooled down on ice for 1 to 2 minutes, and then incubated at 37° C. for 20 minutes to denature and self-hybridize the extended product.

The reactants were added with 2 µl of 10×T4 DNA ligase buffer (500 mM Tris-HCl, 100 mM MgCl₂, 10 mM ATP, 100 mM dithiothreitol (NEB)), and 1 µl of T4 DNA ligase (NEB), were adjusted to a final volume of 20 µl by adding distilled water, and ligated by incubating at 16° C. for 1 hour. The resultant was added with 1 µl of exonuclease I (NEB) and incubated at 37° C. for 30 minutes to remove unligated single stranded DNA.

In order to confirm whether a circular single stranded DNA was synthesized, the reactants were electrophoresed in a 10% denaturing gel, and then the gel was dyed with 1×SYBR® Gold Nucleic Acid Gel Stain (Invitrogen) for 10 minutes. The result is shown in FIG. 2.

Figure 1A:
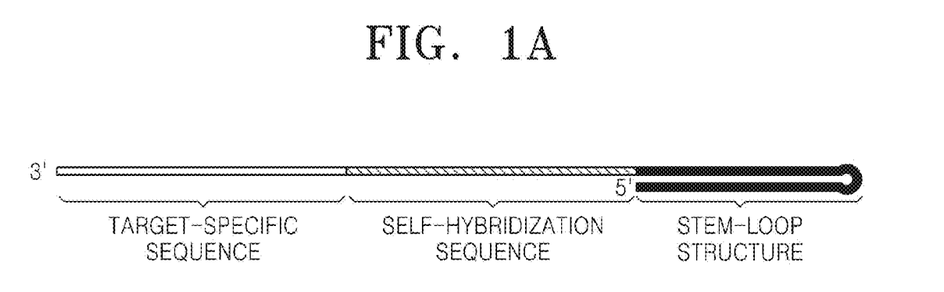
FIG. 1A is a diagram of a primer according to an embodiment of the present disclosure.
Figure 1B:
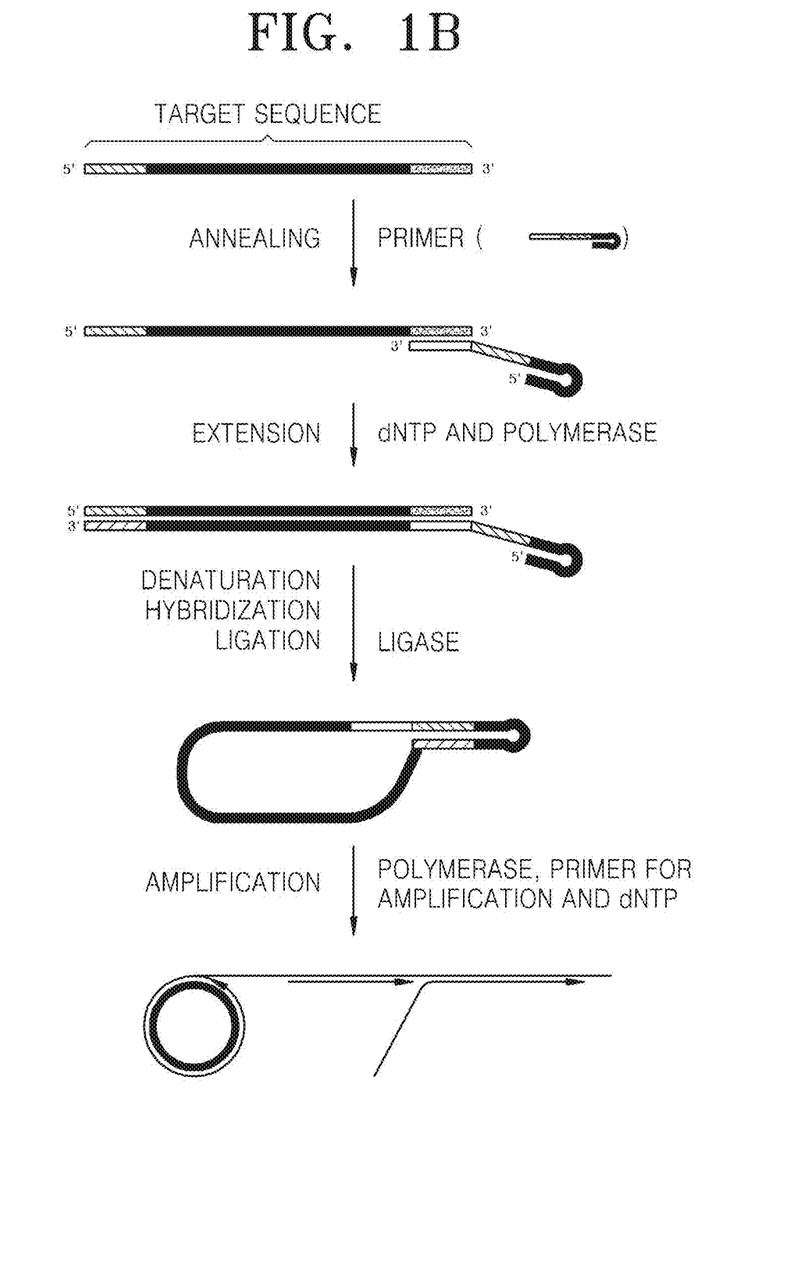
FIG. 1B and FIG. 1C are diagrams of a method of amplifying a target sequence using a primer, according to an embodiment of the present disclosure.
Figure 1C:
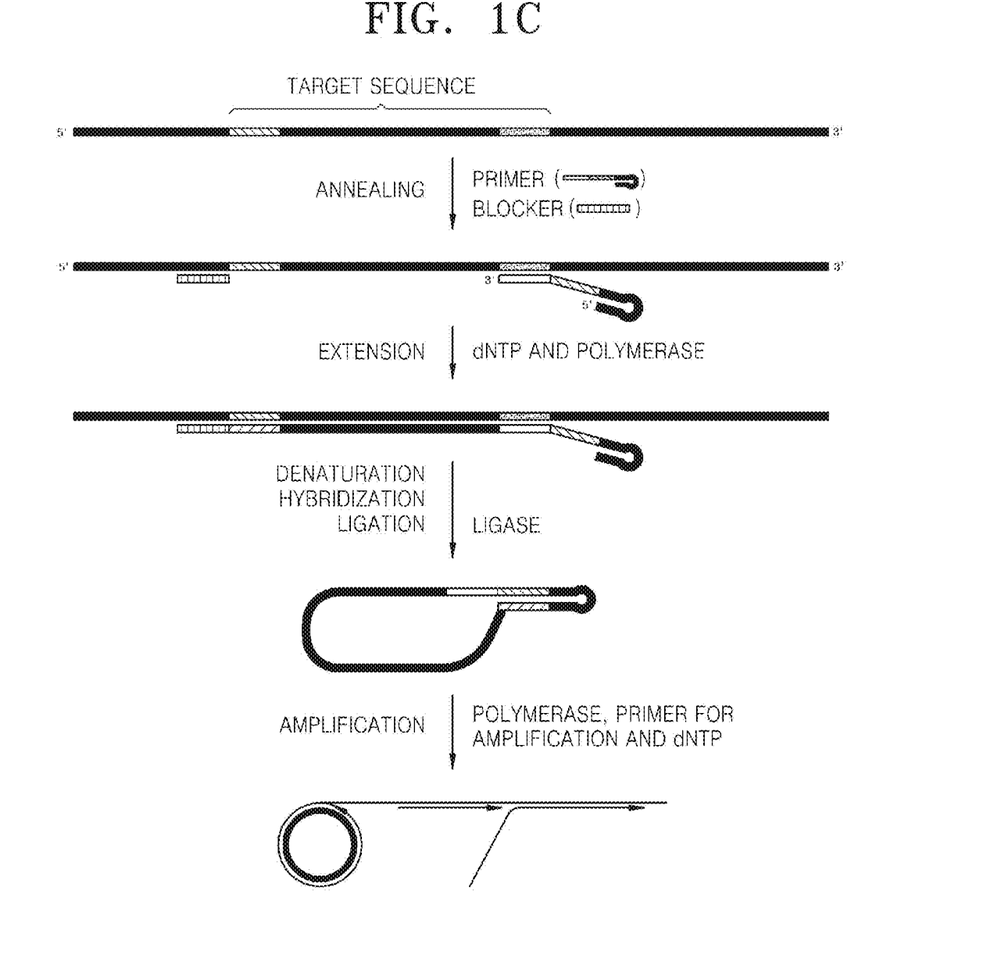
Figure 2:
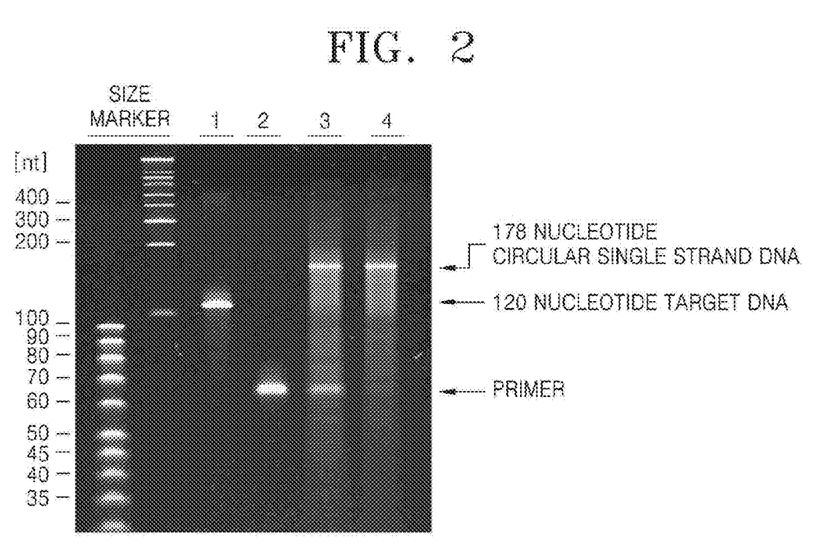
FIG. 2 is a gel image in which a circular extension product prepared according to an embodiment of the present disclosure is confirmed by gel electrophoresis. Lane 1 shows a 120 nt template, lane 2 shows a primer, lane 3 shows an extended and ligated reactant product, and lane 4 shows an extended and ligated reactant product after incubation with exonuclease I.

As shown in FIG. 2, the presence of an extension product (178 nt) obtained by extension and ligation of a target DNA (120 nt) using a primer (78 nt) was observed (lane 3). In addition, the exonuclease I treatment decreased the intensity of the primer band but not that of the extension product (178 nt). Therefore, it was confirmed that the extension product (178 nt) is a circular single stranded DNA (lanes 3 and 4).

Example 2

Amplification of Circular Single Strand DNA

1 µl of the reactant treated with exonuclease I in Example 1 was used for amplification.

In order to amplify various types of targets regardless of the sequence of primers, rolling circle amplification (RCA) was performed using a universal primer complementary to the third region with a stem-loop structure. In addition, in order to increase amplification efficiency, a hyperbranched RCA (i.e., a combination of RCA and MDA) was performed using an RCA primer along with a primer complementary to RCA.

Figure 3A:
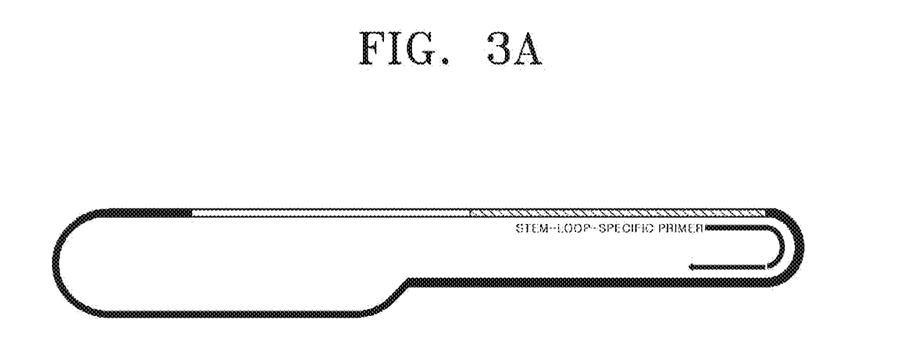
FIG. 3A is a diagram of an amplification primer according to an embodiment of the present disclosure.
Figure 3B:
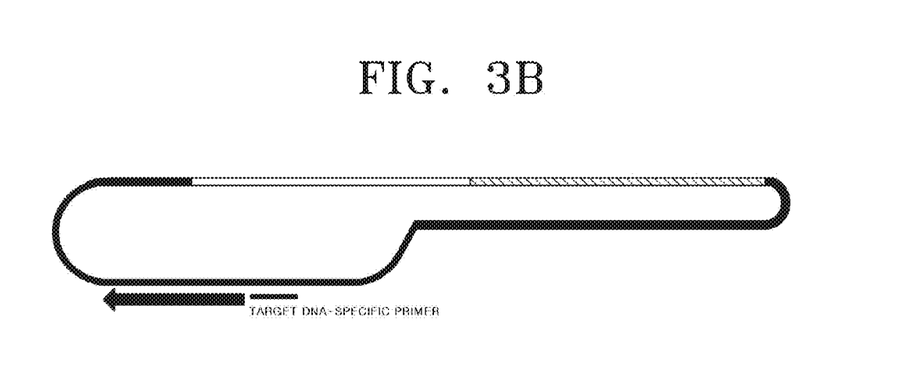
FIG. 3B is a diagram of an amplification primer according to another embodiment of the present disclosure (wherein the arrow indicates an amplifying direction, and the thick solid line indicates an amplification primer).

As for the target sequence-specific primer, RCA and hyperbranched RCA were performed (FIGS. 3A and 3B). More specifically, 1 µl of the reactant, 25 µl of 2× buffer, 0.5 µl of 100 pmol amplification primer, 1 µl of 5% (w/v) Triton X-100, and 0.5 µl of Bst polymerase (NEB) were mixed and adjusted to a final volume of 50 µl by adding distilled water.

The nucleotide sequences of the primers used for amplification are as follows:

```
stem-loop-specific RCA primer:
                                        (SEQ ID NO: 3)
5'-GGGTTGCTGGGGGCGATTGATA-3' stem-loop-specific MDA primer:
                                        (SEQ ID NO: 4)
5'-TATCAATCGCCCCCAGCAACCC-3' target DNA-specific RCA primer:
                                        (SEQ ID NO: 5)
5'-GACGAGTCCGGCCCCTCCATC-3' target DNA-specific MDA primer:
                                        (SEQ ID NO: 6)
5'-GTCCGCCTAGAACATTTGCGG-3'
```

The mixture was incubated at 45° C. for 1 hour. 5 µl of the incubated reactant was mixed with 1 µl of 6× agarose gel loading dye (NEB), and then electrophoresed in a 1% agarose gel under 100 V for 30 minutes. The result of the electrophoresis is shown in FIG. 3C.

Figure 3C:
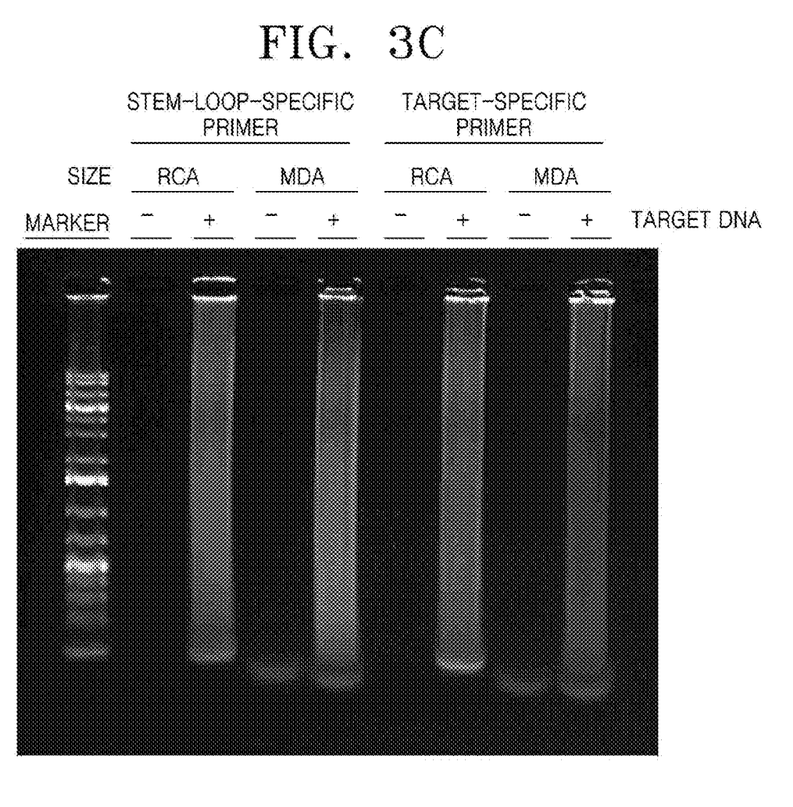
FIG. 3C is a gel image in which a reactant amplified using an amplification primer according to an embodiment of the present disclosure is confirmed by gel electrophoresis.

As shown in FIG. 3C, it was confirmed that both a stem-loop-specific amplification primer and a target DNA-specific amplification primer were suitable for both RCA and hyperbranched RCA reactions.

It should be understood that the exemplary embodiments described therein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of amplifying a target nucleic acid, comprising:
    incubating a primer polynucleotide and a sample comprising a target nucleic acid to form a hybridized product, wherein the primer polynucleotide comprises
        a first region consisting of a sequence of at least two consecutive nucleotides from the 3' terminus thereof that are complementary to at least two consecutive nucleotides of a first region of a target nucleic acid,
        a second region consisting of a sequence of at least two consecutive nucleotides from the 5' terminus of the first region of the primer polynucleotide, wherein the second region is identical to at least two consecutive nucleotides of a second region of the target nucleic acid,
        and a third region beginning from the 5' terminus of the second region of the primer polynucleotide and comprising a stem loop structure,
            wherein the first region of the primer polynucleotide hybridizes to the first region of target nucleic acid, which is located at the 3' terminus from the second region of the target nucleic acid;
    incubating the hybridized product in the presence of a first nucleic acid polymerase to form a extended product having a sequence complementary to the target nucleic acid sequence, wherein the extended product comprises a nucleotide sequence complementary to the second region of the polynucleotide;
    incubating the extended product in the presence of a ligase to form a circular extended product; and
    incubating the circular extended product in the presence of a second nucleic acid polymerase to amplify the target nucleic acid.

2. The method according to claim 1, wherein the first nucleic acid polymerase is a DNA polymerase.

3. The method according to claim 2, wherein the DNA polymerase is DNA polymerase I, Klenow fragment, T4 DNA polymerase, T7 DNA polymerase, or a combination thereof.

4. The method according to claim 1, further comprising cooling off the extended product followed by heating to form a self-hybridized extended product, after forming the extended product.

5. The method according to claim 1, wherein the ligase is DNA ligase.

6. The method according to claim 5, wherein the DNA ligase is T4 DNA ligase, T3 DNA ligase, T7 DNA ligase, *E. coli* DNA ligase, temperature-stable DNA ligase, single-stranded DNA ligase or a combination thereof.

7. The method according to claim 1, further comprising incubating the extended product in the presence of an exonuclease to remove single-stranded DNA, after forming the circular extended product.

8. The method according to claim 1, wherein the second nucleic acid polymerase is DNA polymerase.

9. The method according to claim 8, wherein the DNA polymerase is Bst DNA polymerase, HIV reverse transcriptase, pyrophage 3173 DNA polymerase, Tth polymerase, BcaBEST DNA polymerase, or a combination thereof.

10. The method according to claim 1, wherein the amplifying is performed via isothermal amplification.

11. The method according to claim 10, wherein the isothermal amplification is rolling circle amplification (RCA), strand-displacement amplification (SDA), multiple-displacement amplification (MDA), or a combination thereof.

12. The method according to claim 1, wherein the amplifying is performed in the presence of a primer complementary to the third region of the polynucleotide or a primer complementary to the extended product.

13. The method according to claim 1, further comprising incubating the sample containing a target nucleic acid with a blocking polynucleotide before forming the extended product, wherein the blocking polynucleotide lacks a hydroxyl group at the 3'-terminus thereof and is complementary to at least two consecutive nucleotides from the 5'-terminus of the target nucleic acid.

14. The method according to claim 1, wherein the at least two consecutive nucleotides of the first region of the target nucleic acid includes the 3' terminus of the target nucleic acid.

15. The method according to claim 1, wherein the at least two consecutive nucleotides of the second region of the target nucleic acid includes the 5' terminus of the target nucleic acid.

16. The method according to claim 1, wherein the third region of the primer polynucleotide is phosphorylated at its 5' terminus.

17. The method according to claim 1, wherein the third region of the primer polynucleotide comprises a primer-binding site, a restriction enzyme recognition site, a probe-binding site, or a combination thereof.

* * * * *

SEQUENCE LISTING

```
<160> NUMBER OF SEQ ID NOS: 6

<210> SEQ ID NO 1
<211> LENGTH: 120
<212> TYPE: DNA
<213> ORGANISM: Artificial Sequence
<220> FEATURE:
<223> OTHER INFORMATION: Synthetic (target DNA)

<400> SEQUENCE: 1
ccctatagtg agtcgtatta cagcagatgt ggatcagcaa gcaggagtat gacgagtccg      60 gccccctccat cgtccaccgc aaatgttcta ggcggactat gacttagttg cgttacaccc    120

<210> SEQ ID NO 2
<211> LENGTH: 78
<212> TYPE: DNA
<213> ORGANISM: Artificial Sequence
<220> FEATURE:
<223> OTHER INFORMATION: Synthetic (primer)

<400> SEQUENCE: 2
gggttgctgg gggcgtatca atcgccccca gcaacccccc tatagtgagt cgtattacgg      60
gtgtaacgca actaagtc                                                   78

<210> SEQ ID NO 3
<211> LENGTH: 22
<212> TYPE: DNA
<213> ORGANISM: Artificial Sequence
<220> FEATURE:
<223> OTHER INFORMATION: Synthetic (stem-loop specific primer for
      rolling circle amplification)

<400> SEQUENCE: 3
gggttgctgg gggcgattga ta                                              22
```

```
<210> SEQ ID NO 4
<211> LENGTH: 22
<212> TYPE: DNA
<213> ORGANISM: Artificial Sequence
<220> FEATURE:
<223> OTHER INFORMATION: Synthetic (stem-loop specific primer for
      multiple displacement amplification)

<400> SEQUENCE: 4
tatcaatcgc ccccagcaac cc                                                22

<210> SEQ ID NO 5
<211> LENGTH: 21
<212> TYPE: DNA
<213> ORGANISM: Artificial Sequence
<220> FEATURE:
<223> OTHER INFORMATION: Synthetic (target DNA specific primer for
      rolling circle amplification)

<400> SEQUENCE: 5
gacgagtccg gcccctccat c                                                 21

<210> SEQ ID NO 6
<211> LENGTH: 21
<212> TYPE: DNA
<213> ORGANISM: Artificial Sequence
<220> FEATURE:
<223> OTHER INFORMATION: Synthetic (target DNA specific primer for
      multiple displacement amplification)

<400> SEQUENCE: 6
gtccgcctag aacatttgcg g                                                 21
```